United States Patent
Aparin et al.

(10) Patent No.: US 10,024,818 B2
(45) Date of Patent: Jul. 17, 2018

(54) BIASING OF AN IONIC CURRENT SENSOR

(71) Applicant: QUALCOMM Incorporated, San Diego, CA (US)

(72) Inventors: Vladimir Aparin, San Diego, CA (US); Bo Sun, Carlsbad, CA (US); Joung Won Park, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 222 days.

(21) Appl. No.: 15/186,409

(22) Filed: Jun. 17, 2016

(65) Prior Publication Data

US 2017/0363573 A1 Dec. 21, 2017

(51) Int. Cl.
*G01N 27/414* (2006.01)
*G01N 27/417* (2006.01)

(52) U.S. Cl.
CPC ....... *G01N 27/4145* (2013.01); *G01N 27/417* (2013.01)

(58) Field of Classification Search
CPC ...... G01N 27/00; G01N 27/26; G01N 27/403; G01N 27/414; G01N 27/4145; G01N 27/416; G01N 27/417; G01R 27/00; G01R 27/26
USPC .... 324/71.1; 204/193, 194, 228.1, 242, 400, 204/403.01, 554, 556; 205/775
See application file for complete search history.

(56) References Cited

U.S. PATENT DOCUMENTS

| | | | | |
|---|---|---|---|---|
| 4,293,822 A * | 10/1981 | McFadyen | ........... | H03G 3/3073 330/254 |
| 5,304,950 A | 4/1994 | Martin et al. | | |
| 6,202,474 B1 * | 3/2001 | Takahashi | ............ | G01L 23/221 324/378 |
| 6,222,367 B1 * | 4/2001 | Shimizu | .................. | F02P 17/12 324/378 |
| 6,741,080 B2 * | 5/2004 | Peterson | ................. | F02P 17/12 324/380 |
| 7,001,792 B2 | 2/2006 | Sauer et al. | | |
| 7,750,837 B2 * | 7/2010 | Wang | ..................... | H03F 1/303 341/172 |
| 8,828,208 B2 | 9/2014 | Canas et al. | | |
| 8,986,629 B2 | 3/2015 | Deierling et al. | | |
| 9,034,637 B2 | 5/2015 | Merz et al. | | |
| 2007/0194759 A1 * | 8/2007 | Shimizu | ............... | H02J 7/0016 320/166 |

(Continued)

FOREIGN PATENT DOCUMENTS

WO 2014207877 A1 12/2014

*Primary Examiner* — Hoai-An D Nguyen
(74) *Attorney, Agent, or Firm* — Muncy, Geissler, Olds & Lowe, P.C.

(57) ABSTRACT

An ionic current sensor array includes a master bias generator and a plurality of sensing cells. The master bias generator is configured to generate a bias voltage. Each sensing cell includes an ionic current sensor, an integrating capacitor, a sense transistor coupled between the integrating capacitor and the ionic current sensor, and an amplifier coupled to provide a reference voltage to bias the ionic current sensor. The amplifier includes a first transistor and a second transistor. The first transistor is coupled to receive the bias voltage, and the second transistor is coupled to the first transistor to provide the reference voltage to the ionic current sensor. The second transistor is also coupled between a source of the sense transistor and the gate of the sense transistor.

20 Claims, 5 Drawing Sheets

(56) References Cited

U.S. PATENT DOCUMENTS

2014/0048416 A1  2/2014  Rosenstein et al.

* cited by examiner

BIASING OF AN IONIC CURRENT SENSOR

FIELD OF DISCLOSURE

This disclosure relates generally to ionic current sensors, and in particular, but not exclusively to electronic circuits for the biasing of ionic current sensors.

BACKGROUND

Advances in micro-miniaturization within the semiconductor industry in recent years have enabled biotechnologists to begin packing traditionally bulky sensing tools into smaller and smaller form factors, onto so-called biochips. Despite these advances in micro-miniaturization there remains a need to further miniaturize the chips and/or to increase their throughput. For example, the throughput of many of these chips is, in part, a function of the number of individual sensing cells located on the chip. Thus, many circuit designers attempt to increase the throughput of the system by increasing the number of sensing cells. To maintain a constant sensor chip size, the system designers may resort to reducing the size of each sensing cell. However, reducing the size of each sensing cell can have negative impacts on the performance of the sensor, such as increased noise.

SUMMARY

The following presents a simplified summary relating to one or more aspects and/or embodiments associated with the mechanisms disclosed herein for the biasing of an ionic current sensor. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary presents certain concepts relating to one or more aspects and/or embodiments relating to the mechanisms disclosed herein to bias an ionic current sensor in a simplified form to precede the detailed description presented below.

According to one aspect, an ionic current sensor array includes a master bias generator and a plurality of sensing cells. The master bias generator is configured to generate a bias voltage. Each sensing cell includes an ionic current sensor, an integrating capacitor, a sense transistor coupled between the integrating capacitor and the ionic current sensor, and an amplifier coupled to provide a reference voltage to bias the ionic current sensor. The amplifier includes a first transistor and a second transistor. The first transistor is coupled to receive the bias voltage, and the second transistor is coupled to the first transistor to provide the reference voltage to the ionic current sensor. The second transistor is also coupled between a source of the sense transistor and the gate of the sense transistor.

According to another aspect, a sensing cell includes an ionic current sensor, an integrating capacitor, a sense transistor coupled between the integrating capacitor and the ionic current sensor, and an amplifier coupled to provide a reference voltage to bias the ionic current sensor. The amplifier includes a first transistor and a second transistor. The first transistor is coupled to receive a bias voltage, and the second transistor is coupled to the first transistor to provide the reference voltage to the ionic current sensor. The second transistor is also coupled between a source of the sense transistor and the gate of the sense transistor.

According to yet another aspect, a complementary metal-oxide-semiconductor (CMOS) ionic current sensor array includes a master bias generator, and a plurality of sensing cells. The master bias generator is configured to generate a bias voltage in response to a master reference voltage. Each sensing cell of the plurality of sensing cells includes a bias voltage node coupled to the master bias generator, an ionic current sensor, an integrating capacitor, a sense field effect transistor (FET) having a drain coupled to integrating capacitor and a source coupled to the ionic current sensor, and an amplifier coupled to provide a reference voltage to bias the ionic current sensor. The amplifier includes a first FET and a second FET. The first FET is coupled to the bias voltage node to receive the bias voltage. The second FET is coupled to the first FET to provide the reference voltage to the ionic current sensor. The second FET also includes a drain coupled to a gate of the sense FET, a source coupled to a common reference, and a gate coupled to the source of the sense FET. The reference voltage provided by the amplifier is substantially equal to the master reference voltage.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION

Aspects of the invention are disclosed in the following description and related drawings directed to specific embodiments of the invention. Alternate embodiments may be devised without departing from the scope of the invention. Additionally, well-known elements of the invention will not be described in detail or will be omitted so as not to obscure the relevant details of the invention.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

Figure 1:
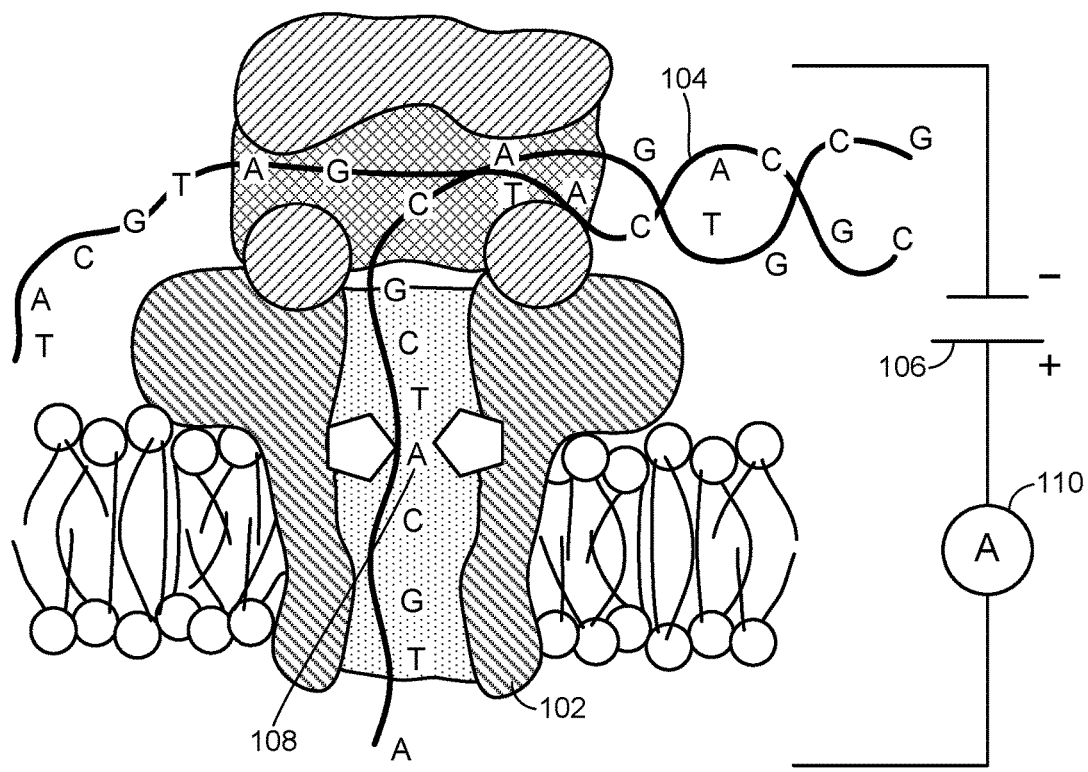
FIG. 1 illustrates an example ionic current sensor configured for the sequencing of a single stranded DNA molecule, in accordance with an aspect of the present disclosure.

FIG. 1 illustrates an example ionic current sensor 102 configured for the sequencing of single stranded DNA (ssDNA) 104. The ionic current sensor 102 is shown as including an opening 108 (also referred to as a "pore"). When configured for rapid nucleotide sequencing, the opening 108 of ionic current sensor 102 may have an internal diameter on the order of a few (e.g., 1, 2, etc.) nanometers. Thus, in these applications, the opening 108 may also be referred to as a "nanopore".

In operation, a voltage potential 106 is applied across the opening 108, which may be immersed in a conducting fluid. When the voltage potential 106 is applied, a small ionic current 110 attributable to the conduction of ions across the opening 108 can be sensed. The amount of ionic current 110 that is sensed is relative to the size (i.e., internal diameter of opening 108). When a molecule, such as a DNA or RNA molecule, passes through the opening 108, it can partially or completely block the opening 108, causing a change in a magnitude of the ionic current 110. It has been shown that such an ionic current blockade can be correlated with the base pair sequence of DNA or RNA molecules.

In practice, nanopore-based DNA sequencers may include a large array of complementary metal-oxide-semiconductor (CMOS) ionic current sensors, such as ionic current sensor 102. Each ionic current sensor of the array may be included in a respective sensing cell that includes electronic circuitry for controlling the operation and monitoring the output of each ionic current sensor 102. For example, each sensing cell may be configured to generate the voltage potential 106 and to sense the ionic current 110 generated by a respective ionic current sensor. In some applications the ionic current 110 is in the range of 10 pA-100 pA. The throughput of such a system is, in part, a function of the number of the sensing cells. To increase the throughput, system designers typically increase the number of sensing cells. However, to maintain a constant sensor chip size, increasing the number of sensing cells can typically only be done by reducing their size.

In some conventional designs, each sensing cell of the array may be designed to have their own operational amplifier (i.e., op-amp) for generating the voltage potential 106. The op-amps may be designed to include multiple gain stages (e.g., differential amplifier, voltage amplifier, output amplifier, etc.). Thus, the op-amps utilized within each sensing cell can be quite large, relative to the overall size of the sensing cell. Furthermore, in an attempt to reduce the size of the sensor chip, reducing the size of the op-amp has a direct correlation to increases in noise generated by the op-amp, and thus, the noise experienced by each sensing cell.

Accordingly, aspects of the present disclosure include a two-transistor amplifier circuit within each sensing cell for the generation of a reference voltage, such as voltage potential 106, of ionic current sensor 102. In one aspect, the two-transistor amplifier circuit occupies a much smaller area on the die when compared to the conventional use of an op-amp. Thus, in some examples, the number of sensing cells included in a sensor chip may be increased without increasing an overall size of the sensor chip. Furthermore, in some examples, aspects of a two-transistor amplifier circuit provides for a reduction in the added noise to the circuitry of each sensing cell.

Figure 2:
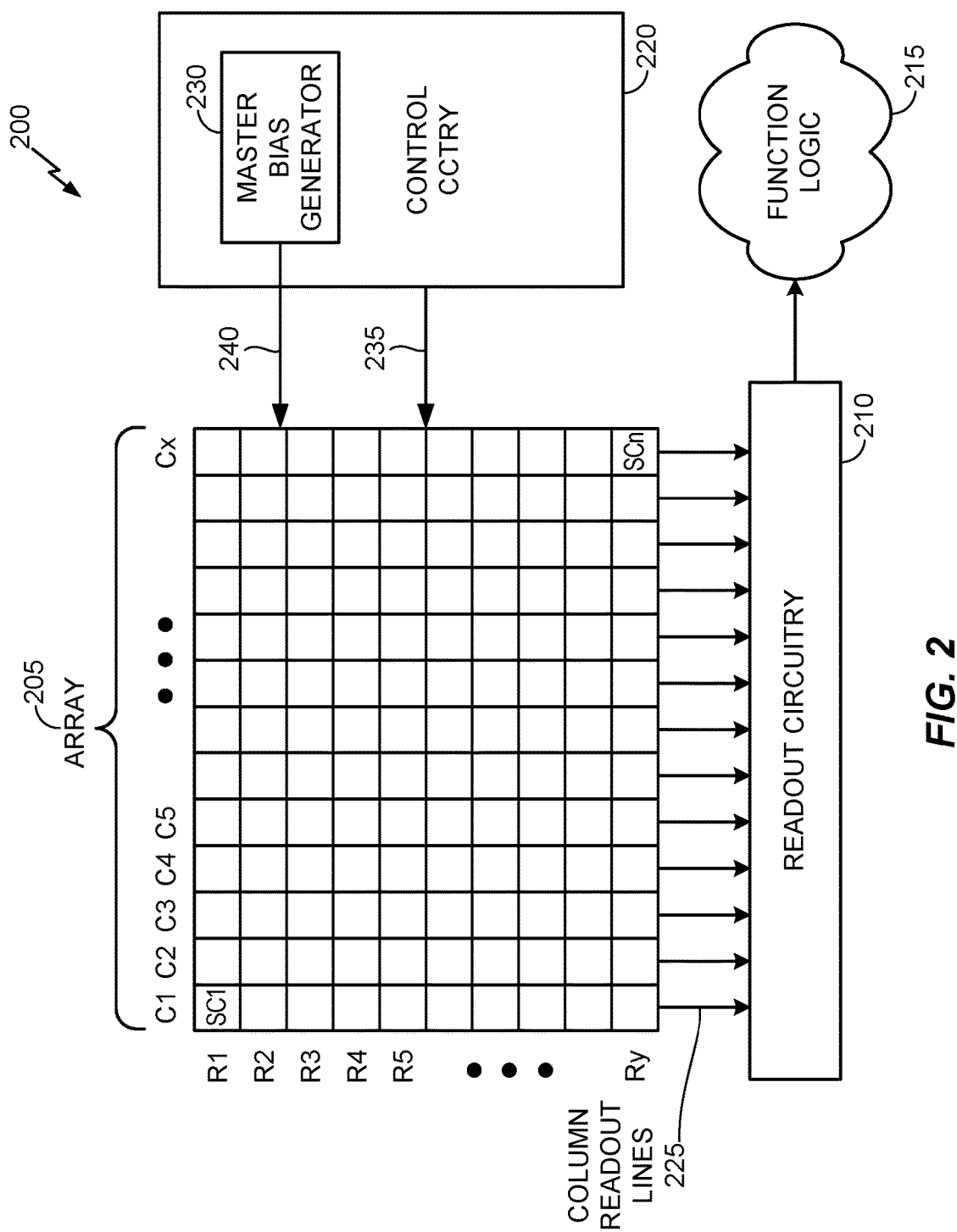
FIG. 2 is a block diagram illustrating an example ionic current sensor array, in accordance with an aspect of the present disclosure.

FIG. 2 is a block diagram illustrating an ionic current sensor array 200, in accordance with an aspect of the present disclosure. The illustrated example of ionic current sensor array 200 includes an array 205, readout circuitry 210, function logic 215, and control circuitry 220.

In one example, array 205 is a two-dimensional array of sensing cells (e.g., sensing cells SC1, . . . , SCn). Each sensing cell may be a complementary metal-oxide-semiconductor ("CMOS") sensing cell, where each sensing cell includes at least one ionic current sensor, such as ionic current sensor 102 of FIG. 1. As illustrated, each sensing cell is arranged into a row (e.g., rows R1 to Ry) and a column (e.g., column C1 to Cx) to sense ionic current through a respective ionic current sensor. In one application, the sensed ionic current can then be used to determine the base pair sequence of DNA and/or RNA molecules.

After each sensing cell has sensed its ionic current, the ionic current data or values are readout by readout circuitry 210 which are then transferred to function logic 215. Readout circuitry 210 may include amplification circuitry, analog-to-digital conversion circuitry, or otherwise. Function logic 215 may simply storage the ionic current values or even analyze the ionic current values to determine the DNA/RNA sequencing. In one example, readout circuitry 210 may readout a row of ionic current values at a time along column readout lines 225 or may readout the ionic current values using a variety of other techniques (not illustrated), such as a serial readout or a full parallel readout of all sensing cells simultaneously.

Control circuitry 220 is coupled to array 205 to control operational characteristics of array 205 via one or more control signals 235. For example, control circuitry 220 may generate a row select, column select, and/or a reset signal for controlling acquisition of the ionic current values by the sensing cells.

As illustrated in FIG. 2, control circuitry 220 may further include a master bias generator 230. Master bias generator 230 is configured to generate a bias voltage 240 that is provided to each sensing cell in the array 205. As will be described in more detail below, each sensing cell of the array 205 may include its own amplifier that receives the bias voltage 240. Each amplifier may then generate a reference voltage for biasing the ionic current sensor within a respective sensing cell. The reference voltage generated by each amplifier may track process and temperature variations to control the sensing speed of the ionic current sensor array 200. The reference voltage may also be adjustable to provide an optimum sensing result. Within each sensing cell of array 205, this reference voltage can be adjusted to reduce the mismatch.

Figure 3A:
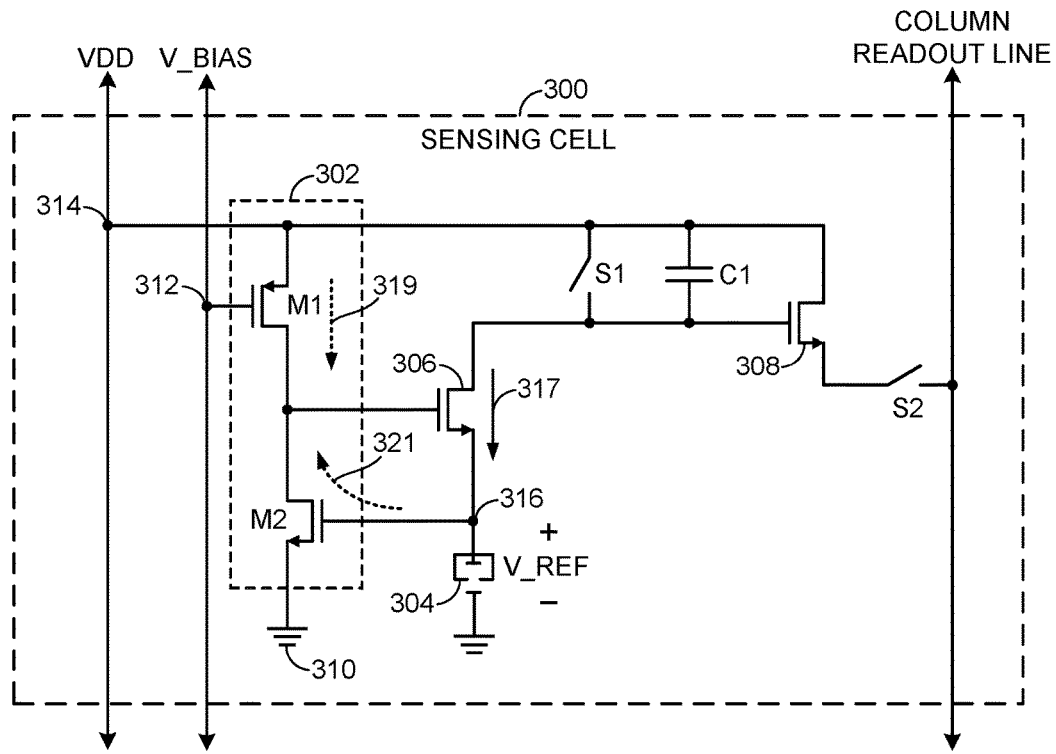
FIG. 3A is a circuit diagram illustrating an example sensing cell, in accordance with an aspect of the present disclosure.

For example, FIG. 3A is a circuit diagram illustrating an example sensing cell 300, in accordance with an aspect of the present disclosure. The illustrated example of sensing cell 300 includes an amplifier 302, an ionic current sensor 304, a sense transistor 306, a buffer transistor 308, a common reference 310, a bias voltage node 312, a supply voltage node 314, a reference voltage node 316, integrating capacitor C1, and switches S1 and S2. Also illustrated in FIG. 3A is an ionic current 317, a current path 319, and feedback path 321. The illustrated example of amplifier 302 is shown as including a first transistor M1 and a second transistor M2.

Sensing cell 300 of FIG. 3A illustrates one possible circuitry architecture for implementing each sensing cell within array 205 of FIG. 2. However, it should be appreciated that embodiments of the present invention are not limited to the illustrated circuitry architectures; rather, one of ordinary skill in the art having the benefit of the instant disclosure will understand that the present teachings are also applicable to various other circuitry architectures.

During a readout operation of the ionic current sensor 304, switch S1 receives a pre-charge signal (not shown) to control switch S1 to pre-charge the integrating capacitor C1 to the supply voltage VDD. In some implementations, switch S1 may be referred to as a reset switch and may include one or more transistors. Amplifier 302 is coupled to provide the reference voltage V_REF to bias the ionic current sensor 304 by way of reference voltage node 316. The sense transistor 306 is coupled between the integrating capacitor C1 and the ionic current sensor 304 such that the ionic current 317 generated by the ionic current sensor 304 is integrated onto integrating capacitor C1 (e.g., by reducing the charge on integrated capacitor C1). In one example, ionic current sensor 304 includes the ionic current sensor 102 of FIG. 1.

Thus, in one example, the voltage across the integrating capacitor C1 is representative of the sensed ionic current 317. In one example, the charge stored in the capacitor is represented by Q=CV, Q is the charge, C is capacitance of capacitor C1 and V is the voltage across the capacitor. The charge is integration of the current over time. Thus, as current is allowed to flow through the capacitor C1, the charge and voltage across the capacitor C1 linearly increases over time. Buffer transistor 308 is configured as a voltage buffer between integrating capacitor C1 and the column readout line. Switch S2 is coupled between the buffer transistor 308 and the column readout line to provide the buffered voltage in response to a transfer signal (not shown). In one example, the pre-charge (i.e., reset) signal applied to switch S1 and the transfer signal applied to switch S2 are provided by way of the control signals 235 generated by control circuitry 220 of FIG. 2.

The transfer signal, the pre-charge (e.g., reset) signal, supply voltage VDD, the bias voltage V_BIAS, and the common reference 310 (e.g., ground) may be routed in the sensing cell 300 by way of metal interconnect layers (i.e., routings) included in the array (e.g., array 205).

Although FIG. 3A illustrates sense transistor 306, buffer transistor 308, and transistor M1 and M2 as field effect transistors (FETs), other transistor types may be implemented for one or more of the illustrated transistors, including, but not limited to bipolar junction transistors (BJTs).

As mentioned above, amplifier 302 is configured to provide the reference voltage V_REF to bias the ionic current sensor 304. As shown in FIG. 3A, the amplifier 302 is a two-transistor amplifier circuit. In one example, amplifier 302 consists of the first transistor M1 and the second transistor M2. For example, the illustrated example of amplifier 302 does not include any additional transistors other than the first transistor M1 and the second transistor M2. Furthermore, the illustrated example of amplifier 302 does not include an operational amplifier (op-amp).

FIG. 3A illustrates the first transistor M1 as coupled to the bias voltage node 312 to receive the bias voltage V_BIAS. As will be described in more detail below, the bias voltage node 312 may be coupled to the master bias generator (e.g., master bias generator 230 of FIG. 2) to receive the bias voltage V_BIAS. In one example, the first transistor M1 is configured as a current source to provide a current path 319 between the supply voltage node 314 and the gate of the sense transistor 306. In particular, the first transistor M1 is shown as including a gate coupled to the bias voltage node 312, a source coupled to the supply voltage node 314 and a drain coupled to the gate of the sense transistor 306. In one example, the magnitude of the current provided along current path 319 by the first transistor M1 is responsive to a magnitude of the bias voltage V_BIAS.

As further shown in FIG. 3A, the second transistor M2 is coupled to provide a feedback path 321 between the source and gate of the sense transistor 306. In one example, the second transistor M2 is configured as a common-source amplifier. More, particularly, the second transistor M2 is shown as including a gate coupled to the source of the sense transistor 306, a source coupled to a common reference 310 of the sensing cell 300, and a drain coupled to the gate of the sense transistor 306. In one example, the common reference 310 is a common voltage potential to several components of the sensing cell 300 and may include ground, or a voltage potential other than ground. In one example, the reference voltage V_REF is the voltage at reference voltage node 316 with respect to the common reference 310. Thus, the reference voltage V_REF used to bias the ionic current sensor 304 may be with respect to ground. However, in another example, the common reference 310 may be biased to a non-zero voltage potential (e.g., V1), where the voltage at voltage reference node 316 is greater than voltage V1.

Figure 3B:
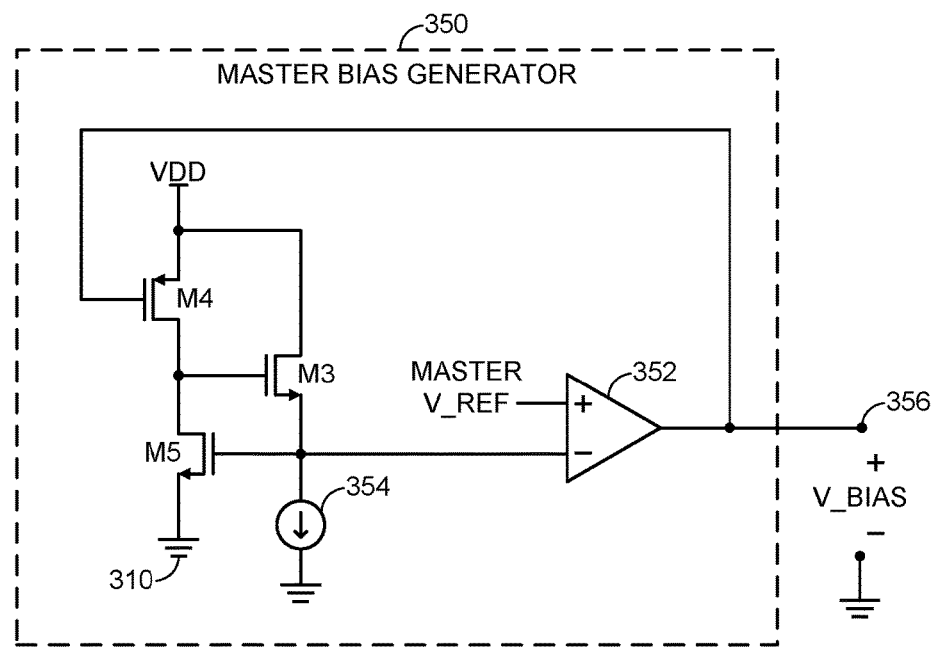
FIG. 3B is a circuit diagram illustrating an example master bias generator, in accordance with an aspect of the present disclosure.

FIG. 3B is a circuit diagram illustrating an example master bias generator 350, in accordance with an aspect of the present disclosure. The illustrated example of master bias generator 350 includes a master bias amplifier 352, a current source 354, a third transistor M3, a fourth transistor M4, a fifth transistor M5, and a master bias voltage node 356.

Master bias generator 350 of FIG. 3B illustrates one possible circuitry architecture for implementing the master bias generator 230 of FIG. 2. However, it should be appreciated that embodiments of the present invention are not limited to the illustrated circuitry architectures; rather, one of ordinary skill in the art having the benefit of the instant disclosure will understand that the present teachings are also applicable to various other circuitry architectures.

As shown in FIG. 3B, the master bias amplifier 352 is coupled to receive a master reference voltage (e.g., MASTER V_REF) at an input of the master bias amplifier 352. In one example, master bias amplifier 352 is configured as a differential amplifier to provide the bias voltage V_BIAS to master bias voltage node 356 in response inputs received at a non-inverting input and inverting inputs of the master bias amplifier 352. The third transistor M3, fourth transistor M4, and fifth transistor M5 are coupled to provide a feedback path between the output and the input (e.g., inverting input) of the master bias amplifier 352.

The third transistor M3, fourth transistor M4, and fifth transistor M5 are also shown as coupled together in a same arrangement as that of the sense transistor 306, first transistor M1, and second transistor M2, respectively of sensing cell 300. For example, the third transistor M3 (corresponding to the sense transistor 306) is shown as including a gate coupled to the drain of the fourth transistor M4 (corresponding to the first transistor M1), a source coupled to the gate of the fifth transistor M5 (corresponding to the second transistor M2), and a drain coupled to the source of the fourth transistor M4. Similarly, the fourth transistor M4 is shown as including a gate coupled to the master bias voltage node 356 (corresponding to the bias voltage node 312), a source coupled to the supply voltage VDD, and a drain coupled to the gate of the gate of the third transistor M3. The fifth transistor M5 is shown as including a gate coupled to the source of the third transistor M3, a source coupled to the common reference 310, and a drain coupled to the gate of the third transistor M3.

Furthermore, in one example, the size of the third, fourth, and fifth transistors may be scaled to the sizes of the sense, first, and second transistors, respectively of the sensing cell 300. That is, a size of the third transistor M3 may be scaled to the size of the sense transistor 306, a size of the fourth transistor M4 may be scaled to the size of the sense first transistor M1, and a size of the fifth transistor M5 may be scaled to the size of the second transistor M2. The scaling of transistors may provide for the relative mirroring of one or more signals (e.g., currents) through the transistors of the master bias generator 350 to those through the transistors of the amplifiers 302 included in each sensing cell 300.

Figure 4A:
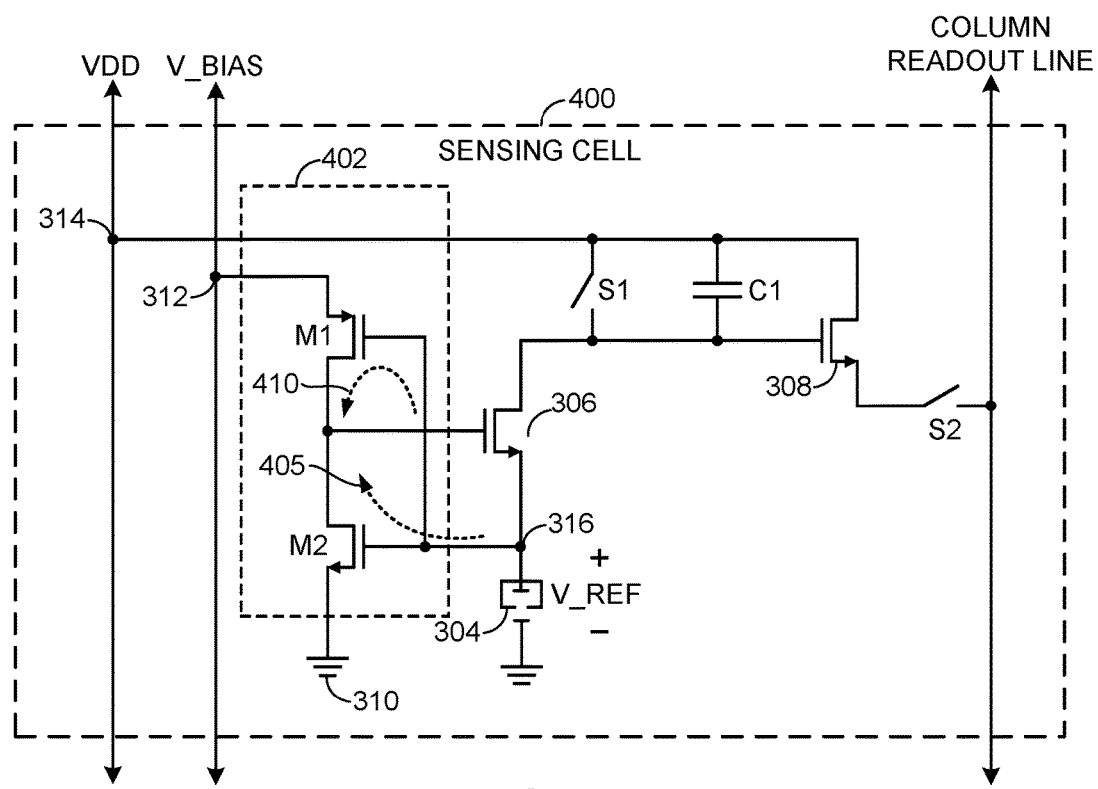
FIG. 4A is a circuit diagram illustrating another example sensing cell, in accordance with an aspect of the present disclosure.

FIG. 4A is a circuit diagram illustrating another example sensing cell 400, in accordance with an aspect of the present disclosure. Sensing cell 400 of FIG. 4A illustrates one possible circuitry architecture for implementing each sensing cell within array 205 of FIG. 2.

The illustrated example of sensing cell 400 is similar to the sensing cell 300 of FIG. 3A, where like numerals are used to refer to like elements. However, sensing cell 400 includes an amplifier 402 having a different circuit arrangement than that of the amplifier 302 of sensing cell 300. Amplifier 402 is a two-transistor amplifier circuit similar to that of amplifier 302, including both a first transistor M1 and a second transistor M2. However, in the illustrated example of FIG. 4A, both the first transistor M1 and the second transistor M2 are included in a feedback path between the source and gate of the sense transistor 306. For example, the second transistor M2 is shown as providing a first feedback path 405, while the first transistor M1 is shown as providing a second feedback patch 410.

In particular, the first transistor M1 is shown in FIG. 4A as including a gate coupled to the source of sense transistor 306, a source coupled to the bias voltage node 312, and a drain coupled to the gate of the sense transistor 306. FIG. 4A also illustrates the second transistor M2 as including a gate coupled to the source of the sense transistor 306, a source coupled to the common reference 310, and a drain coupled to the gate of the sense transistor 306. In one aspect, the circuit configuration of first transistor M1 and second transistor M2, in amplifier 402 may further reduce the sensing transistor's (i.e., sense transistor 306) noise to the circuitry of the sensing cell 400 by providing strong negative feedback.

Figure 4B:
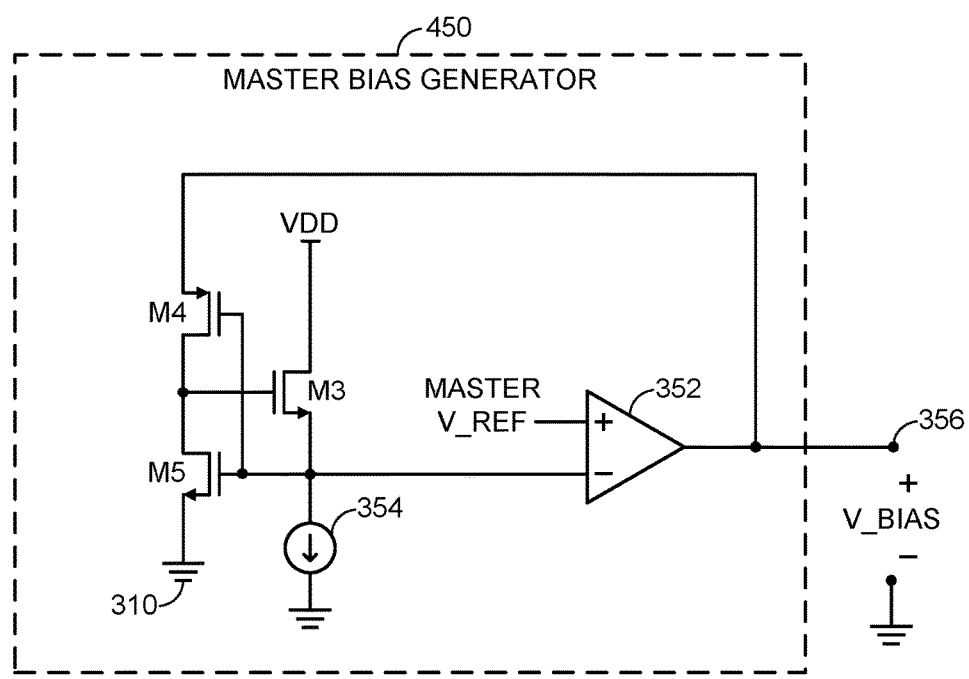
FIG. 4B is a circuit diagram illustrating another example master bias generator, in accordance with an aspect of the present disclosure.

FIG. 4B is a circuit diagram illustrating another example master bias generator 450, in accordance with an aspect of the present disclosure. The master bias generator 450 of FIG. 4B illustrates one possible circuitry architecture for implementing the master bias generator 230 of FIG. 2. The illustrated example of master bias generator 450 is similar to the master bias generator 350 of FIG. 3B, where like numerals are used to refer to like elements. However, master bias generator 450 includes third transistor M3, fourth transistor M4, and fifth transistor M5 coupled together in a different circuit arrangement than that shown in FIG. 3B. In particular, the circuit arrangement of transistors M3, M4, and M5 match the circuit arrangement of the corresponding sense, first, and second transistors of sensing cell 400. Thus, the master bias generator 450 may be utilized for generating the bias voltage V_BIAS, when the amplifiers of the sensing cells are implemented using the circuit arrangement of amplifier 402.

For example, the third transistor M3 (corresponding to the sense transistor 306) is shown as including a gate coupled to the drain of the fourth transistor M4 (corresponding to the first transistor M1), a source coupled to the gate of the fifth transistor M5 (corresponding to the second transistor M2), and a drain coupled to the supply voltage VDD. Similarly, the fourth transistor M4 is shown as including a gate coupled to the gate of the fifth transistor M5, a source coupled to the master bias voltage node 356, and a drain coupled to the gate of the gate of the third transistor M3. The fifth transistor M5 is shown as including a gate coupled to the source of the third transistor M3, a source coupled to the common reference 310, and a drain coupled to the gate of the third transistor M3.

Figure 5:
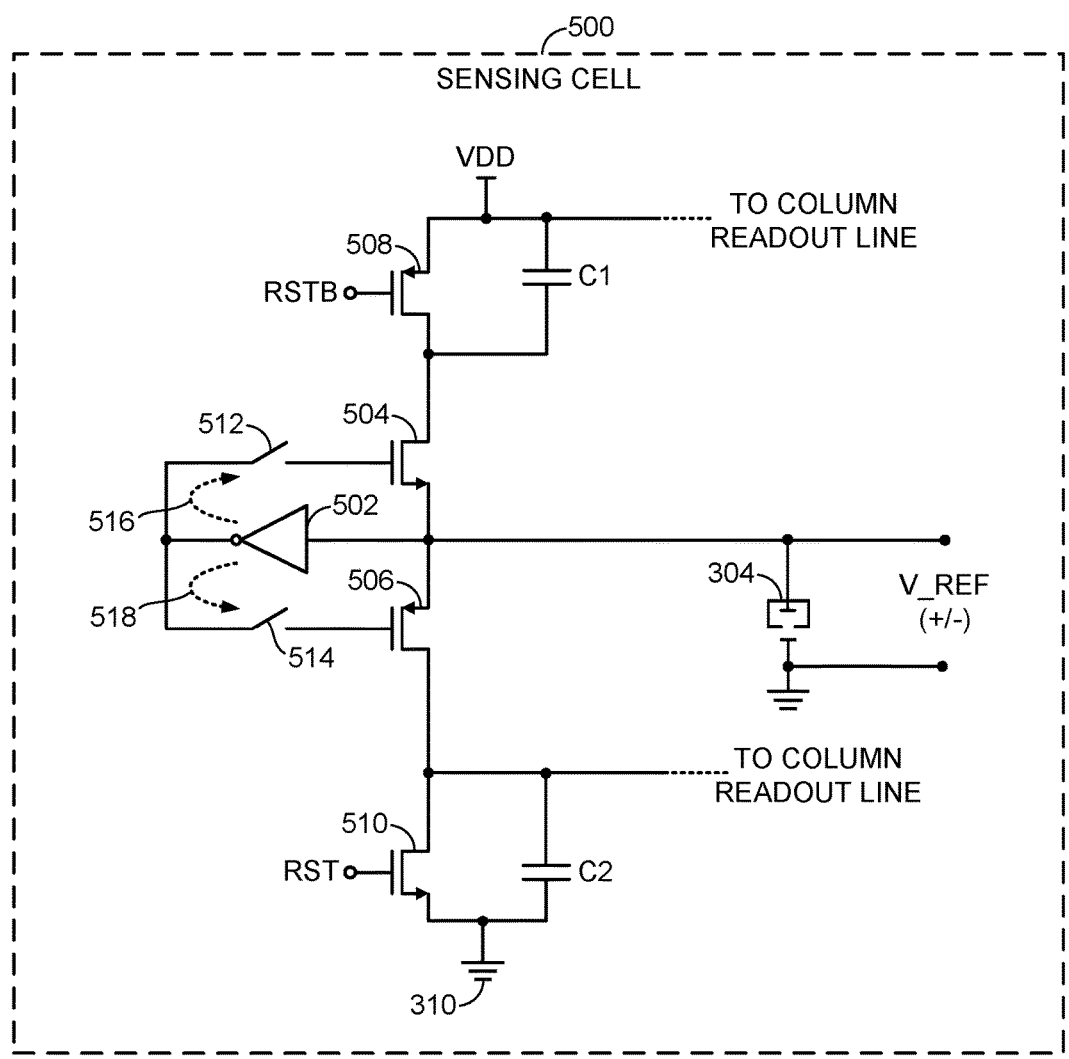
FIG. 5 is a circuit diagram illustrating yet another example sensing cell, in accordance with an aspect of the present disclosure.

FIG. 5 is a circuit diagram illustrating yet another example sensing cell 500, in accordance with an aspect of the present disclosure. The illustrated example of sensing cell 500 includes an amplifier 502, an ionic current sensor 304, a first integrating capacitor C1, a second integrating capacitor C2, a first sense transistor 504, a second sense transistor 506, a first reset transistor 508, a second reset transistor 510, a first switch 512, and a second switch 514. Also illustrated in FIG. 5 is a first feedback path 516 and a second feedback path 518.

Sensing cell 500 of FIG. 5 illustrates one possible circuitry architecture for implementing each sensing cell within array 205 of FIG. 2. Amplifier 502 may be implemented using any of the aforementioned amplifier circuits including amplifier 302 of FIG. 3A or amplifier 402 of FIG. 4A. However, amplifier 502 is coupled to selectively switch between providing a positive reference voltage and a negative reference voltage to bias the ionic current sensor 304. This provides an option to perform the sequencing in both directions. When operating in the negative direction, a depleted electrode can be recovered.

During a readout operation of the ionic current sensor 304, control circuitry (e.g., control circuitry 220) determines whether the sensing cell 500 should utilize a positive reference voltage V_REF or a negative reference voltage V_REF to bias the ionic current sensor 304. If it determines that a positive reference voltage V_REF should be utilized, the control circuitry 220 may provide a reset signal RSTB to the first reset transistor 508 to reset the voltage on the first integrating capacitor C1 to the supply voltage VDD. The control circuit 220 may then send one or more control signals 240 to close switch 512 (and open switch 514) to couple the output of amplifier 502 to the gate of the first sense transistor 504, thereby providing feedback path 516 between the source and gate of first sense transistor 504. When switch 512 is closed, the amplifier 502 provides a positive reference voltage V_REF to the ionic current sensor 304. The ionic current is then integrated onto the first integrating capacitor C1 through the first sense transistor 504, and then readout to the column readout line through one or more voltage buffers and/or switches (not shown).

If the control circuitry 220 determines that a negative reference voltage V_REF should be utilized, the control circuitry 220 may provide a reset signal RST to the second reset transistor 510 to reset the voltage on the second integrating capacitor C2 to the common reference 310. The control circuit 220 may then send one or more control signals 240 to close switch 514 (and open switch 512) to couple the output of amplifier 502 to the gate of the second sense transistor 506, thereby providing feedback path 518 between the source and gate of second sense transistor 506. When switch 514 is closed, the amplifier 502 provides a negative reference voltage V_REF to the ionic current sensor 304. The ionic current is then integrated onto the second integrating capacitor C2 through the second sense transistor 506, and then readout to the column readout line through one or more voltage buffers and/or switches (not shown).

In one example, the channel conductivity of the first sense transistor 504 may be opposite that of the channel conductivity of the second sense transistor 506. For example, as shown in FIG. 5, the first sense transistor 504 may be an n-channel FET, while the second sense transistor 506 may be a p-channel FET. Similarly, the first reset transistor 508 may have a channel conductivity that is the opposite of the channel conductivity of the second reset transistor 510. For example, as shown in FIG. 5, the first reset transistor 508 may be a p-channel FET, while the second reset transistor 510 may be an n-channel FET.

Those of skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The methods, sequences and/or algorithms described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor.

Accordingly, an aspect of the present disclosure can include a computer readable media embodying a method for reading out one or more ionic current values from an ionic current sensor array. Accordingly, the invention is not limited to illustrated examples and any means for performing the functionality described herein are included in embodiments of the invention.

While the foregoing disclosure shows illustrative embodiments of the invention, it should be noted that various changes and modifications could be made herein without departing from the scope of the invention as defined by the appended claims. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated.

What is claimed is:

1. An ionic current sensor array, comprising:
   a master bias generator configured to generate a bias voltage; and
   a plurality of sensing cells, wherein each sensing cell of the plurality of sensing cells includes:
      an ionic current sensor;
      an integrating capacitor;
      a sense transistor coupled between the integrating capacitor and the ionic current sensor; and
      an amplifier coupled to provide a reference voltage to bias the ionic current sensor, wherein the amplifier comprises:
         a first transistor coupled to receive the bias voltage; and
         a second transistor coupled to the first transistor to provide the reference voltage to the ionic current sensor and coupled between a source of the sense transistor and the gate of the sense transistor.

2. The ionic current sensor array of claim 1, wherein the second transistor is coupled to provide a feedback path between the source of the sense transistor and the gate of the sense transistor.

3. The ionic current sensor array of claim 2, wherein each sensing cell of the plurality of sensing cells comprises:
   a bias voltage node coupled to the master bias generator to receive the bias voltage; and
   a supply voltage node coupled to receive a supply voltage, wherein the first transistor is coupled to the bias voltage node and the supply voltage node and is configured as a current source to provide a current path between the supply voltage node and the gate of the sense transistor.

4. The ionic current sensor array of claim 3, wherein the first transistor comprises:
   a gate coupled to the bias voltage node;
   a source coupled to the supply voltage node; and
   a drain coupled to the gate of the sense transistor, and wherein the second transistor comprises:
   a gate coupled to the source of the sense transistor;
   a source coupled to a common reference of a respective sensing cell; and
   a drain coupled to the gate of the sense transistor.

5. The ionic current sensor array of claim 2, wherein both the first transistor and the second transistor are included in the feedback path between the source of the sense transistor and the gate of the sense transistor.

6. The ionic current sensor array of claim 5, wherein each sensing cell of the plurality of sensing cells comprises a bias voltage node coupled to the master bias generator to receive the bias voltage, wherein the first transistor comprises:
   a gate coupled to the source of the sense transistor;
   a source coupled to the bias voltage node; and
   a drain coupled to the gate of the sense transistor, and wherein the second transistor comprises:
   a gate coupled to the source of the sense transistor;
   a source coupled to a common reference of a respective sensing cell; and
   a drain coupled to the gate of the sense transistor.

7. The ionic current sensor array of claim 1, wherein the master bias generator comprises:
   a master bias amplifier coupled to receive a master reference voltage and to generate the bias voltage in response thereto, wherein reference voltage provided by the amplifier of each of the plurality of sensing cells is substantially equal to the master reference voltage.

8. The ionic current sensor array of claim 7, wherein the master bias generator further comprises a third transistor, a fourth transistor, and a fifth transistor coupled to provide a feedback path between an output of the master bias amplifier and an input of the master bias amplifier, wherein the third transistor, the fourth transistor, and the fifth transistor are coupled together in a same arrangement as that of the sense transistor, the first transistor, and the second transistor, respectively, included in each of the plurality of sensing cells.

9. The ionic current sensor array of claim 8, wherein:
   a size of the third transistor is scaled to a size of at least one of the sense transistors included in a respective sensing cell,
   a size of the fourth transistor is scaled to a size of at least one of the first transistors included in the respective sensing cell, and
   a size of the fifth transistor is scaled to a size of at least one of the second transistors included in the respective sensing cell.

10. The ionic current sensor array of claim 1, wherein the amplifier is coupled to selectively switch between providing a positive reference voltage and a negative reference voltage to bias the ionic current sensor.

11. The ionic current sensor array of claim 10, wherein the integrating capacitor is a first integrating capacitor of a respective sensing cell, and wherein the sense transistor is a first sense transistor of the respective sensing cell, wherein each sensing cell of the plurality of sensing cells further comprises:
   a second integrating capacitor;
   a second sense transistor coupled between the second integrating capacitor and the ionic current sensor;
   a first switch configured to selectively couple the amplifier to the gate of the first sense transistor; and
   a second switch configured to selectively couple the amplifier to a gate of the second sense transistor.

12. The ionic current sensor array of claim 11, wherein:
   the first sense transistor comprises an n-channel field effect transistor (FET), and
   the second sense transistor comprises a p-channel FET.

13. The ionic current sensor array of claim 1, wherein the amplifier consists of the first transistor and the second transistor.

14. A sensing cell, comprising:
   an ionic current sensor;
   an integrating capacitor;
   a sense transistor coupled between the integrating capacitor and the ionic current sensor; and
   an amplifier coupled to provide a reference voltage to bias the ionic current sensor, wherein the amplifier comprises:
   a first transistor coupled to receive a bias voltage; and
   a second transistor coupled to the first transistor to provide the reference voltage to the ionic current sensor and coupled between a source of the sense transistor and the gate of the sense transistor.

15. The sensing cell of claim 14, wherein the second transistor is coupled to provide a feedback path between the source of the sense transistor and the gate of the sense transistor.

16. The sensing cell of claim 15, wherein the sensing cell further comprises:
   a bias voltage node coupled to a master bias generator to receive the bias voltage; and
   a supply voltage node coupled to receive a supply voltage, wherein the first transistor is coupled to the bias voltage node and the supply voltage and is configured as a current source to provide a current path between the supply voltage node and the gate of the sense transistor.

17. The sensing cell of claim 15, wherein both the first transistor and the second transistor are included in the feedback path between the source of the sense transistor and the gate of the sense transistor.

18. The sensing cell of claim 14, wherein the amplifier is coupled to selectively switch between providing a positive reference voltage and a negative reference voltage to bias the ionic current sensor.

19. The sensing cell of claim 18, wherein the integrating capacitor is a first integrating capacitor, and wherein the sense transistor is a first sense transistor, wherein the sensing cell further comprises:
   a second integrating capacitor;
   a second sense transistor coupled between the second integrating capacitor and the ionic current sensor;
   a first switch configured to selectively couple the amplifier to the gate of the first sense transistor; and
   a second switch configured to selectively couple the amplifier to a gate of the second sense transistor.

20. A complementary metal-oxide-semiconductor (CMOS) ionic current sensor array, comprising:
   a master bias generator configured to generate a bias voltage in response to a master reference voltage; and
   a plurality of sensing cells, wherein each sensing cell of the plurality of sensing cells includes:
   a bias voltage node coupled to the master bias generator;
   an ionic current sensor;
   an integrating capacitor;
   a sense field effect transistor (FET) having a drain coupled to integrating capacitor and a source coupled to the ionic current sensor; and
   an amplifier coupled to provide a reference voltage to bias the ionic current sensor, wherein the amplifier comprises:
   a first FET coupled to the bias voltage node to receive the bias voltage; and
   a second FET coupled to the first FET to provide the reference voltage to the ionic current sensor, wherein the second FET comprises a drain coupled to a gate of the sense FET, a source coupled to a common reference, and a gate coupled to the source of the sense FET, wherein the reference voltage is substantially equal to the master reference voltage.

* * * * *